US009512451B2

(12) United States Patent
Lali et al.

(10) Patent No.: US 9,512,451 B2
(45) Date of Patent: Dec. 6, 2016

(54) ENZYMATIC PROCESS FOR FAT AND OIL HYDROLYSIS

(71) Applicants: Arvind Mallinath Lali, Mumbai (IN); Annamma Anil Odaneth, Mumbai (IN); Rajesh Natwarlal Vadgama, Mumbai (IN); Anuradha Devdas Bhat, Mumbai (IN); Amit Pande, Mumbai (IN); Mrunal Anil Warke, Mumbai (IN)

(72) Inventors: Arvind Mallinath Lali, Mumbai (IN); Annamma Anil Odaneth, Mumbai (IN); Rajesh Natwarlal Vadgama, Mumbai (IN); Anuradha Devdas Bhat, Mumbai (IN); Amit Pande, Mumbai (IN); Mrunal Anil Warke, Mumbai (IN)

(73) Assignee: Institute of Chemical Technology (Deemed University), Mumbai (IN)

( * ) Notice: Subject to any disclaimer, the term of this patent is extended or adjusted under 35 U.S.C. 154(b) by 119 days.

(21) Appl. No.: 14/375,380

(22) PCT Filed: Jan. 30, 2013

(86) PCT No.: PCT/IB2013/000110
§ 371 (c)(1),
(2) Date: Jul. 29, 2014

(87) PCT Pub. No.: WO2013/114178
PCT Pub. Date: Aug. 8, 2013

(65) Prior Publication Data
US 2015/0010966 A1    Jan. 8, 2015

(30) Foreign Application Priority Data
Jan. 30, 2012   (IN) ............................ 278/MUM/2012

(51) Int. Cl.
*C12P 7/64*   (2006.01)

(52) U.S. Cl.
CPC ............... *C12P 7/6418* (2013.01); *C12P 7/64* (2013.01)

(58) Field of Classification Search
CPC ............................... C12P 7/64; C12P 7/6418
See application file for complete search history.

(56) References Cited

U.S. PATENT DOCUMENTS

| 5,116,745 A | 5/1992 | Mazur et al. |
| 5,932,458 A | 8/1999 | Piazza, Jr. |
| 6,500,974 B2 | 12/2002 | Thengumpillil et al. |

FOREIGN PATENT DOCUMENTS

| NL | EP 0232933 A1 * | 8/1987 | ............. C11C 1/045 |
| WO | WO 90/04033 | 4/1990 | |
| WO | WO 90/13656 | 11/1990 | |
| WO | WO 91/16442 | 10/1991 | |
| WO | WO 2012/122826 | 9/2012 | |

OTHER PUBLICATIONS

Zuyi L. et al., "Stability of Microbial Lipase in Alcoholysis of Fish Oil During Repeated Enzyme Use", Biotechnology Letters, Apr. 1993, vol. 15, No. 4, pp. 393-398.*
Shibasaki-Kitakawa N. et al., High quality biodiesel fuel production from crude Jatropha oil without upstream and downstream processing, AIChE—Proceedings, ABST/Article 264g, 2011 Annual Meeting, Minneapolis, Originally prsented on Oct. 18, 2011; published on the web at—http://www3.aiche.org/proceedings/Abstract.aspx?PaperID=233225, pp. 1-7.*
Ataya F. et al., "Acid-catalyzed transesterification of Canola oil to biodiesel under single- and two-phase reaction conditions", Energy & Fuel, 2007, vol. 21, pp. 2450-2459.*
Rajendran A. et al., "Lipase catalyzed ester synthesis for food processing industries", Brazilian Archives of Biology and Technology, Jan.-Feb. 2009, vol. 52, No. 1, pp. 207-219.*
Hill K., "Fats and oils as oleochemical raw materials," *Pure Appl. Chem.*, 72(7):1255-1264 (2000).
Baumann et al., "Natural Fats and Oils—Renewable Raw Materials for the Chemical Industry," *Angew. Chem. Int. Ed. Engl.*, 27(1):41-62 (1988).
Lee, et al., "Oat (*Avena sativa*) Caryopses as a Natural Lipase Bioreactor," JAOCS, 67(11):761-765 (1990).
Gutierrez-Ayesta, et al., "Relation between lipase structures and their catalytic ability to hydrolyse triglycerides and phospholipids," *Enzyme and Microbial Technology*, 41:35-43 (2007).
Tan et al., "Preparation of PVA/chitosan lipase membrane reactor and its application in synthesis of monoglyceride," *Journal of Molecular Catalysis B: Enzymatic*, 18:325-331 (2002).
Fernandes et al., "Hydrolysis and synthesis reactions catalysed by *Thermomyces lanuginosa*, lipase in the AOT/Isooctane reversed micellar system," *Journal of Molecular Catalysis B: Enzymatic*, 30:43-49 (2004).
Bilyk et al., "Lipase-Catalyzed Triglyceride Hydrolysis in Organic Solvent," JAOCS, 68(5):320-323 (1991).
Shamel et al., "Hydrolysis of palm and olive oils by immobilised lipase using hollow fibre reactor," *Biochemical Engineering Journal*, 34:228-235 (2007).
Goswami et al., "Surfactant enhanced ricinoleic acid production using *Candida rugosa* lipase," *Bioresource technology*, 101:6-13 (2010).

(Continued)

*Primary Examiner* — Satyendra K Singh
(74) *Attorney, Agent, or Firm* — Brinks Gilson & Lione

(57) ABSTRACT

An efficient process for enzymatic hydrolysis of fats and oils in a homogenous mixture is provided herein. The present invention in particular provides a process for production of fatty acids, sn-regio mono-acylglycerol (MAG), sn-regio di-acyl-glycerols (DAG), and glycerol from fats, wherein more than 98% fats can be converted into the desired product. The present invention also provides a process for the production of fatty acids and glycerol, virtually free of sn-regio diacyl-glycerols (DAG) and comprising less than 5% sn-regio mono-acylglycerol (MAG) in the end product.

16 Claims, 7 Drawing Sheets

(56) References Cited

OTHER PUBLICATIONS

Martinez et al., "Effect of Water on Canola Oil Hydrolysis in an Online Extraction—Reaction System Using Supercritical $CO_2$," *Ind. Eng. Chem. Res*, 41:6475-6481 (2002).

Sovova et al., "Lipase-catalysed hydrolysis of blackcurrant oil in supercritical carbon dioxide," *Chemical Engineering Science*, 58:2339-2350 (2003).

Pastor et al., "Enzymatic Preparation of Mono- and Di-Stearin by Glycerolysis of Ethyl Stearate and Direct Esterification of Glycerol in the Presence of a Lipase from *Candida Antarctica* (Novozym 435)," *Biocatalysis and Biotransformation*, 12(2):147-157 (1995).

Xu et al., "Effects of Lipid-Borne Compounds on the Activity and Stability of Lipases in Microaqueous Systems for the Lipase-Catalyzed Interesterification," *Stability and Stabilization of Biocatalysts*, Elsevier Science B.V., pp. 441-446 (1998).

Vacek et al., "Lipase-mediated hydrolysis of blackcurrant oil," *Enzyme and Microbial Technology*, 27:531-536 (2000).

He et al., "Lipase-catalyzed hydrolysis of olive oil in chemically-modified AOT/isooctane reverse micelles in a hollow fiber membrane reactor," *Biotechnology Letters*, 23:1257-1262 (2001).

Murty et al., "Hydrolysis of rice bran oil using an immobilized lipase from *Candida rugosa* in isooctane," *Biotechnology Letters*, 26:563-567 (2004).

Freitas et al., "Enzymatic hydrolysis of soybean oil using lipase from different sources to yield concentrated of polyunsaturated fatty acids," *World J Microbiol Biotechnol*, 23:1725-1731 (2007).

Goswami, et al., "Optimization of Process Varibles in Castor Oil Hydrolysis by *Candida Rugosa* Lipase with Buffer as Dispersion Medium," *Biotechnology and Bioprocess Engineering*, 14:220-224 (2009).

Kahveci, et al., "Upgrading of Farmed Salmon Oil Through Lipase-Catalyzed Hydrolysis," *The Open Biotechnology Journal*, 4:47-55 (2010).

Cavalcanti-Oliveira et al., "Study of Soybean Oil Hydrolysis Catalyzed by *Thermomyces lanuginosus* Lipase and Its Application to Biodiesel Production via Hydroesterification," *Enzyme Research*, 2011:1-8 (2011).

Kulkarni et al., "Enzymatic hydrolysis of castor oil: An approach for rate enhancement and enzyme economy," *Indian Journal of Biotechnology*, 4:241-245 (2005).

Bhat et al., "Enzymatic hydrolysis of castor oil in tertiary butanol," *8th Euro Fed Lipid Congress*, Munich, Germany (Nov. 2010) www.eurofedlipid.org/meetings/archive/munich/5873/5873_0344.pdf.

International Search Report received in related Application No. PCT/IB2013/000110 dated May 14, 2013.

\* cited by examiner

ENZYMATIC PROCESS FOR FAT AND OIL HYDROLYSIS

RELATED APPLICATIONS

The present patent document is a §371 filing based on PCT Application Serial No. PCT/IB2013/000110, filed Jan. 30, 2013, designating the United States and published in English, which claims priority from Indian provisional application number 278/MUM/2012, filed on Jan. 30, 2012. All of the foregoing applications are hereby incorporated by reference.

FIELD OF INVENTION

The present invention relates to an efficient and cost effective process for production of oleochemicals such as fatty acids and glycerol from fats.

BACKGROUND OF THE INVENTION

Oils and fats are triglycerides which typically consist of glycerol and saturated and unsaturated fatty acids. These are being increasingly used in recent times for the development of competitive, powerful products, which are both consumer-friendly and environment-friendly (Hill K, *Pure and Applied Chemistry* 72 (2000) pp. 1255-1264). For most of the further uses, oils and fats must be split into the so-called oleochemical base materials, predominantly fatty acids and glycerol. Intermediates as well as monoacyl glycerols (MAG's), diacylglycerols (DAG's), fatty acid methyl esters and also hydrogenation products of the fatty acid methyl esters i.e. fatty alcohols find immense use in the oleochemical industry (Falbe et al., *Angew. Chem. Int. Ed. Engl.,* 27 (1988) pp. 41-62).

The hydrolysis of triacylglycerols (TAG) to yield free fatty acids (FAs), MAGs and glycerol is the primary reaction, the fatty acids thus produced are further interesterified, transesterified, or are converted into high-value fatty alcohols. These base materials are then used as intermediates in production of washing and cleansing agents, cosmetics, surfactants, polymers and lubricants. There are many useful mono-glycerides of immense commercial interest like glycerol monostearates, monooleates and monoricinoleates that are produced synthetically from fatty acids and glycerol to the tune of more than 10,000 tons annually.

Hydrolysis of oil has been accomplished commercially by using catalysts at high temperature and high pressure like Twitchell process and Colgate-Emery process. Colour development, formation of by-products, induction of polymerization and requirement of subsequent distillation are major drawbacks of these processes. The reaction by-products are associated with undesired dark colour and burnt taste, and thus need specialized techniques (e.g. molecular distillation) to remove colour and by-products. The rapid advances in the field have led to the introduction of milder chemical reaction conditions for fat-splitting; however, the process is still very high on CAPEX and calls for better technologies.

Hydrolysis of oils or fats, specifically with lipase as biocatalyst, provides several advantages including reaction at atmospheric pressure and low temperatures. There are several additional advantages of the enzymatic process in addition to the possibility of controlling the reaction to give MAGs. However, till date fat splitting through the use of lipolytic enzymes has been carried out only in experimental trials. Enzymatic process has never been commercialized due to high cost and long reaction times.

Hammond et al. (*Journal of American Oil Chemist's Society*, 67 (1990), pp. 761-765) describe 90% lipolysis in about 58 days where, only 10% conversion was achieved in 4 days. The authors postulate that the slow rate of hydrolysis may be due to inhibition of the enzyme by glycerol, a product of the reaction. U.S. Pat. No. 5,932,458 describes use of lipase catalysts recovered from pulverised seeds for splitting of fats and oils of various types, differing in the degree of saturation or hydroxylation.

Microbial lipase has also been studied as catalyst of hydrolysis of sunflower oil, soybean lecithin and their mixtures at 60° C. in a biphasic mixture heptane-buffer pH 7.0 (Ferreira et al., *Enzyme and Microbial Technology*, 41(1-2) 2007, pp. 35-43). Hydrolysis of palm oil with an yield of 32-50% of MAGs using membrane bound lipase in a two-phase reaction system (Tianwei Tan et al., *Journal of Molecular Catalysis B: Enzymatic*, 18 (2002), pp. 325-331). Fernandesa M L M et al. (*Journal of Molecular Catalysis B. Enzymatic*, 30 (1) 2004, pp. 43-49) describes hydrolysis and synthesis reactions catalysed by TLL lipase in the AOT/Isooctane reversed micellar system. Bilyk et al. (*Journal of American Oil Chemist's Society*, 68 (1991), pp. 320-323) report 76% hydrolysis by use of fungal lipases in presence of secondary amines, at moderate temperatures within 20 hrs. Further improvements in the yields have also been reported at 45° C.

Kulkarni et al. (*Indian Journal of Biotechnology*, 4 (2005), pp. 241-245) report optimization of enzymatic hydrolysis of castor oil with reference to reactor and reaction conditions. Ramachandran et al. (*Biochemical Engineering Journal*, 34 (2007), pp. 228-235) describes use of packed bed reactors with immobilized lipases for studying kinetics of hydrolysis of different oils and for improving the operational stability of lipases used in hydrolysis reactions. Goswami et al. (*Bioresource technology*, 101 (1) 2010, pp. 6-13) describes surfactant enhanced hydrolysis of castor oils for production of fatty acids. Martinez et al. describes hydrolysis of canola oil in a continuous flow of supercritical $CO_2$ through a packed-bed reactor (*Biocatalysis and Biotransformation*, 12 (2) 2002, pp. 147-157). Helena Sovova et al. describes hydrolysis of blackcurrant seed oil catalysed by Lipozyme in a packed-bed reactor using supercritical $CO_2$ (*Chemical Engineering Science*, 58 (11) 2003, pp. 2339-2350).

WO 91/016442 and U.S. Pat. No. 5,116,745 describe a process for the selective hydrolysis of triglycerides to 2-acyl glycerides. The process uses a primary lower alkyl alcohol, an aqueous buffer system and a 1,3-lipase. The 2-acyl monoglycerides can be used to make stereospecific 1,2-diacyl glycerides or 2,3-diacyl glycerides through esterification with acid anhydrides and 1,3-lipase catalysis. Stereospecific triglycerides can be made from these materials by standard esterification reactions under conditions which control rearrangement.

WO90/013656 describes a two-step enzymatic process involving lipase-catalyzed transesterification of triglycerides followed by low-temperature crystallization for preparing oil based products significantly enriched in omega-3 fatty acids. The process yields a mixture of highly pure monoglycerides, at least 60% of which contain omega-3 fatty acids. WO 90/04033 describes a process for the production of high purity monoglycerides by lipase-catalyzed transesterification. The method described comprises combining oils or pure triglycerides with alcohol, a small amount of water and a lipase. The reaction proceeds under mild conditions, and produces high yields of beta-monoglyceride product.

U.S. Pat. No. 6,500,974 describes a process for the preparation of a monoglyceride by reacting a fatty acid and glycerol in the presence of a food grade polar solvent and avoiding the use of catalysts. Eitel Pastor et al. (*Biocatalysis and Biotransformation,* 12 (2) 1995, pp. 147-157) describes direct esterification of glycerol with stearic acid or transesterification using ethyl stearate as acyl donor in the presence of *Candida antarctica* lipase (Novozym-435) using a variety of solvents of differing polarity.

In almost all cases, the hydrolysis was either incomplete or required longer reaction time which is more than three days to achieve completion. The effectiveness of lipases as catalysts is often offset by the high costs of production and isolation so that research groups are constantly striving to increase the yields of enzymes or productivity of enzymes. Further, commercial applications have been limited by high enzyme consumption, long reaction times and low productivity that have impeded successful industrial application.

Typically, lipase catalyzed enzymatic hydrolysis has been carried out using oil in water or water in oil emulsions where, the reusability of enzyme solution poses a problem if enzyme is used in free form. Also, immobilized enzyme preparations suffer from substrate accessibility issues wherein poor diffusibility of substrate in a non-homogeneous media restricts its efficient conversion.

None of the methods of the prior art provides the three desirable attributes namely, low cost of enzyme catalyst, complete hydrolysis of the oil and high enzyme stability. In the cited prior arts, no attempts have been made to separate the incompletely hydrolyzed oils (MAGs and DAGs) and FAs.

All the reports on enzymatic monoglyceride synthesis is primarily focused on the glycerolysis of various substrates like castor oil, soybean oil, coconut oil, palm oil, rapeseed oil, rice bran using glycerol. MAG production via glycerolysis using different oils and glycerol is an expensive process.

Therefore, there is a need to develop an efficient process for production of oleochemicals such as fatty acids and glycerol from oils. The process may be a process of hydrolysis of oils and/or fats, which bypasses the glycerol mediated hydrolysis i.e. glycerolysis and results in higher of fatty acids, MAGs directly through controlled oil hydrolysis.

Additional aspects of the disclosure will be set forth in part in the description which follows, and in part will be obvious from the description, or may be learned by practicing the invention. The invention is set forth and particularly pointed out in the appended claims, and the present disclosure should not be construed as limiting the scope of the claims in any way. The following detailed description includes exemplary representations of various embodiments of the invention, which are not restrictive of the invention, as claimed. The accompanying figures constitute a part of this specification and, together with the description, serve only to illustrate various embodiments and not limit the invention.

Citation of various references in this application, is not an admission that these references are prior art to the invention.

None of the enzymatic hydrolysis processes disclosed in the art describe the formation of a homogenous mixture of oil and water. Additionally, the processes are extremely time consuming and the hydrolysis takes up to 72 hours for completion. Hence there is a need in the art for a quick and easier process for enzymatic hydrolysis of fats and oils in a homogenous mixture.

The present invention provides an enzyme catalyzed process for the hydrolysis of fats, oils and combinations of fats and oils which can be completed in under 6 hours.

SUMMARY OF THE INVENTION

Accordingly the present invention provides a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol.

Also, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG).

BRIEF DESCRIPTION OF ACCOMPANYING DRAWINGS

The following drawings form part of the present specification and are included to further illustrate aspects of the present invention. The invention may be better understood by reference to the drawings in combination with the detailed description of the specific embodiments presented herein.

DETAILED DESCRIPTION OF THE INVENTION

Figure 1:
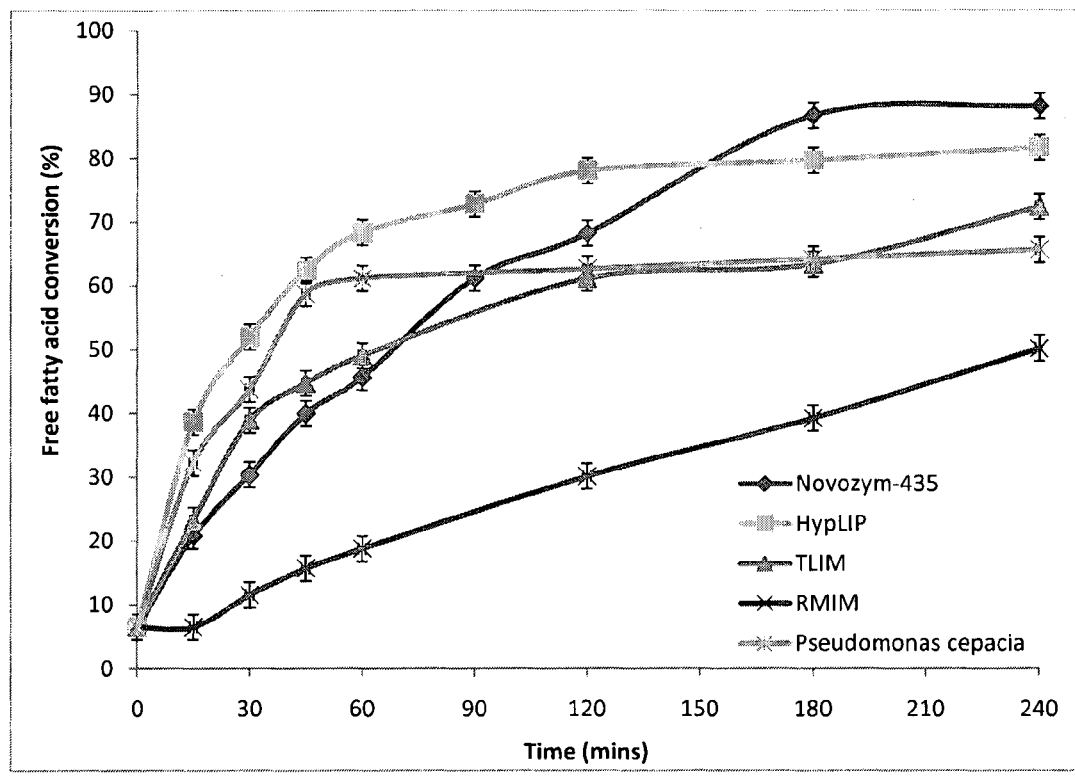
FIG. 1 shows the hydrolysis of castor oil with different lipases in homogenous media.
Figure 2:
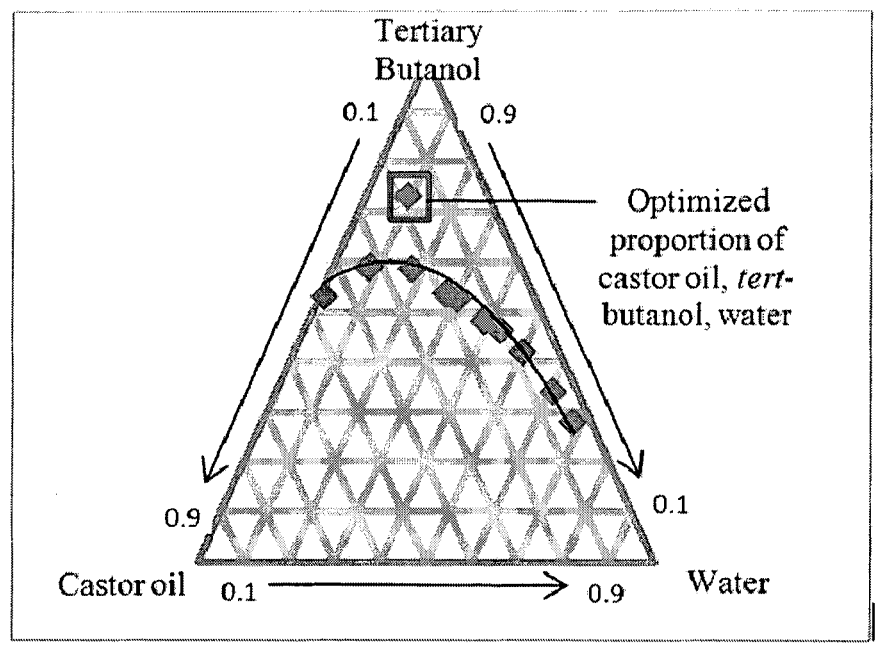
FIG. 2 shows the ternary phase diagram of castor oil, t-butanol and water.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

DEFINITIONS

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The articles "a", "an" and "the" are used to refer to one or to more than one (i.e., to at least one) of the grammatical object of the article.

The terms "comprise" "comprising" "including" "containing" "characterized by" and grammatical equivalents thereof are used in the inclusive, open sense, meaning that additional elements may be included. It is not intended to be construed as "consists of only."

As used herein, "consisting of" and grammatical equivalent thereof exclude any element, step or ingredient not specified in the claim.

The term "oleochemical" used herein refers to the substances derived from plant, microbial or animal fat. Example of oleochemical includes but not limited to fatty acids, fatty acid methyl esters (FAME), fatty alcohols, fatty amines, glycerols, alcohol ethoxylates, alcohol sulfates, alcohol ether sulfates, quaternary ammonium salts, monoacylglycerols (MAG), diacylglycerols (DAG), structured triacylglycerols (TAG), sugar esters, and other oleochemical products.

The term "polar organic solvent" used in the present invention refers to organic solvents that allow ionization of the solute in the dissolving medium.

The term "fats" should be attributed to its broadest meaning so as to include oils, fats and lipids. The term "fats" used in the present specification refers to triglycerides, triesters of glycerol and any of several fatty acids.

The term "regioselective enzyme" as used herein means selectivity of an enzyme with respect to position of fatty acid on the glycerol backbone in the lipid.

The term "regioselective enzyme" and "specific enzyme" can be used interchangeably.

The term "substrate mixture" refers to a single phase system (homogenous mixture) comprising fat, oil or mixture thereof, a polar organic solvent and water, wherein the term substrate mixture can be interchangeably used with the term "reaction mixture".

The present invention is not to be limited in scope by the specific embodiments described herein, which are intended for the purposes of exemplification only. Functionally-equivalent products, compositions, and methods are clearly within the scope of the invention, as described herein.

The present invention relates to an efficient and cost effective process for production of oleochemicals such as fatty acids, glycerols and/or sn-regio mono-acyl glycerols (sn-regio MAG isomers) from oils, fats or mixtures thereof. These products of hydrolysis have immense potential in the oleochemical industry.

The present invention in particular discloses an efficient process of hydrolysis of oils, fats or mixture thereof by employing immobilized lipase(s) and a single phase substrate mixture, wherein a polar organic solvent is used to solubilize oil into water. The invention further discloses a hydrolysis process comprising multiple steps by which the hydrolysis process can be controlled to obtain fatty acids, glycerine yield and/or sn-regio monoacyl glycerols.

Furthermore, the methodology disclosed in the present invention results in enhanced reusability and stability of the enzymes in the chosen medium i.e. an immobilized lipase.

The process for production of oleochemical as disclosed in the present invention comprises subjecting a single phase system comprising a substrate mixture to a first enzymatic hydrolysis to obtain a partial hydrolysate, subjecting the partial hydrolysate to a cation exchange resin to obtain a first product, subjecting the first product to a second enzymatic hydrolysis to obtain a second product, and separating oleochemical/fatty acids from the a first product or second product by distilling the said product to obtain concentrated product mixture and to recover the organic solvent, recovering the free fatty acids and glycerol from the said concentrated product by centrifugation or extraction method employing non-polar water immiscible organic solvent, wherein the substrate mixture is prepared by mixing fat, oil or a mixture thereof with water and a polar organic solvent, wherein the enzyme is immobilized.

The use of polar organic solvent disclosed in the present specification allows the formation of a homogenous mixture of fats with water which can be acted upon by lipase to produce the homogenate on completion of the hydrolysis reaction.

The process for production of fatty acids, sn-regio monoacylglycerol (MAG), sn-regio diacyl-glycerols (DAG), and glycerol from fats undergoes complete hydrolysis in two hours and the process for production of fatty acids and glycerol from fatty acids, sn-regio mono-acylglycerol (MAG), sn-regio diacyl-glycerols (DAG), and glycerol which can be obtained from the first enzymatic hydrolysis disclosed herein requires three hours for completion. Hence the complete hydrolysis of fats to fatty acids and glycerol can be completed in less than six hours.

The second step of hydrolysis disclosed in the present specification involving the hydrolysis of fatty acids, sn-regio mono-acylglycerol (MAG), sn-regio diacyl-glycerols (DAG), and glycerol from fats to fatty acids and glycerol allows the hydrolysis products to be produced virtually free of sn-regio diacyl-glycerols (DAG) with only minute traces of the compound being present in the end product. The major reaction products observed are fatty acids and glycerol, with sn-regio mono-acylglycerol (MAG) comprising less than 5% of the hydrolysis products.

An embodiment of the present invention provides a process for production of fatty acids, sn-regio mono-acyl-glycerol (MAG), sn-regio diacyl-glycerois (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol.

In an embodiment of the present invention, there is provided a process for production of fatty acids and glycerol comprising subjecting the hydrolysate comprising fatty acids, sn-regio mono-acylglycerol (MAG), sn-regio diacyl-glycerols (DAG), and glycerol with an ion exchange resin followed by another enzymatic hydrolysis with lipase to obtain a mixture, wherein the mixture comprises fatty acids and glycerol, and wherein the mixture has less than 5% mono-acylglycerol (MAG).

In another embodiment of the present invention, there is provided a process for production of fatty acids and glycerol comprising subjecting said hydrolysate comprising fatty acids, sn-regio mono-acylglycerol (MAG), sn-regio diacyl-glycerols (DAG), and glycerol with a solid acid catalyst followed by another enzymatic hydrolysis with lipase to obtain a mixture, wherein the mixture comprises fatty acids and glycerol, and wherein said mixture has less than 5% mono-acylglycerol (MAG).

Another embodiment of the present invention provides a process for production of fatty acids and glycerol comprising subjecting said hydrolysate comprising fatty acids, sn-regio mono-acylglycerol (MAG), sn-regio diacyl-glycerols (DAG), and glycerol with a solid acid catalyst followed by another enzymatic hydrolysis with lipase to obtain a mixture, wherein the mixture comprises fatty acids and glycerol, and wherein said mixture has less than 5% mono-acylglycerol (MAG), wherein the solid acid catalyst is selected form the group consisting of zeolites, clays, cation acid ion exchange resins, SO$_4$-oxides, amorphous mixed oxides, and heteropoly acids.

In yet another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the fat is oil.

In another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the fat is oil selected from the group consisting of vegetable oil, tree borne oil, microbial oil, animal origin oil, fish oil, castor oil, olive oil, mustard oil, linseed oil, canola oil, coconut oil, coriander oil, corn oil, cottonseed oil, hazelnut oil, olive oil, neem oil, palm oil, peanut oil, rapeseed oil, rice bran oil, safflower oil, soybean oil, sunflower seed oil, and mixtures thereof.

Another embodiment of the present invention provides a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the fat is selected from the group consisting of saturated fat, unsaturated fat, hydroxyl unsaturated fat, hydroxyl saturated fat, epoxy fat, phospholipids, wax esters, and mixtures thereof.

In still another embodiment of the present invention there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the fat is a fatty acid based polyol esters.

In yet another embodiment of the invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the polar organic solvent is selected from the group consisting of t-butanol, iso-amyl alcohol, di-acetone alcohol, ethanol, propanol, and t-pentanol, and mixtures thereof.

In another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the enzymatic hydrolysis with lipase are carried out with immobilized lipase.

Another embodiment of the present invention provides a process for production of fatty acids and glycerol comprising subjecting the hydrolysate comprising fatty acids, sn-regio mono-acylglycerol (MAG), sn-regio diacyl-glycerols (DAG), and glycerol with an ion exchange resin followed by another enzymatic hydrolysis with lipase to obtain a mixture, wherein the mixture comprises fatty acids and glycerol, and wherein the mixture has less than 5% mono-acylglycerol (MAG), wherein the enzymatic hydrolysis with lipase are carried out with immobilized lipase.

In yet another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the enzymatic hydrolysis with lipase are carried out with immobilized lipase immobilized on a support, wherein the base material of the support is selected from the group consisting of co-polymer of polystyrene and divinyl benzene, polyacrylic, polystyrene, and polymethacrylate.

In another embodiment of the present invention, there is provided a process for production of fatty acids and glycerol comprising subjecting the hydrolysate comprising fatty acids, sn-regio mono-acylglycerol (MAG), sn-regio diacyl-glycerols (DAG), and glycerol with an ion exchange resin followed by another enzymatic hydrolysis with lipase to obtain a mixture, wherein the mixture comprises fatty acids and glycerol, and wherein the mixture has less than 5% mono-acylglycerol (MAG), wherein the enzymatic hydrolysis with lipase are carried out with immobilized lipase immobilized on a support, wherein the base material of the support is selected from the group consisting of co-polymer of polystyrene and divinyl benzene, polyacrylic, polystyrene, and polymethacrylate.

Another embodiment of the present invention provides a process for production of fatty acids and glycerol comprising subjecting the hydrolysate comprising fatty acids, sn-regio mono-acylglycerol (MAG), sn-regio diacyl-glycerols (DAG), and glycerol with an ion exchange resin followed by another enzymatic hydrolysis with lipase to obtain a mixture, wherein the mixture comprises fatty acids and glycerol, and wherein the mixture has less than 5% mono-acylglycerol (MAG), wherein the ion exchange resin is a strongly acidic cation exchange resin.

Yet another embodiment of the present invention provides a process for production of fatty acids and glycerol comprising subjecting the hydrolysate comprising fatty acids, sn-regio mono-acylglycerol (MAG), sn-regio diacyl-glycerols (DAG), and glycerol with an ion exchange resin followed by another enzymatic hydrolysis with lipase to obtain a mixture, wherein the mixture comprises fatty acids and glycerol, and wherein the mixture has less than 5% mono-acylglycerol (MAG), wherein the ion exchange resin is a strongly acidic cation exchange resin selected from the group consisting of sulphonated polymeric resins, Indion™130, Indion™140, Indion™190, Indion™770, DIAION® SK1B, DIAION® SK104, DIAION® SK110, DIAION® SK112, DIAION® SK116, DIAION® PK208, DIAION® PHK212, DIAION® PK216, DIAION® PK220, DIAION® PK228, and DIAION® HPK25.

In still another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the enzymatic hydrolysis with lipase is carried out at a temperature ranging from 30° C. to 80° C.

Another embodiment of the present invention provides a process for production of fatty acids, sn-regio mono-acyl-glycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the enzymatic hydrolysis with lipase is carried out at a temperature ranging from 50 to 65° C., preferably 60° C.

In yet another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the process results in more than 99% conversion of the fat to fatty acids, sn-regio mono-acylglycerol (MAG), sn-regio diacyl-glycerols (DAG) and glycerol.

In still another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the process results in more than 99% conversion of the TAGS (triacyl glycerols) present in the fats to fatty acids, sn-regio mono-acylglycerol (MAG), sn-regio diacyl-glycerols (DAG) and glycerol.

In yet another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the homogenous mixture comprises fat, a polar organic solvent and water in the ratio of 1:4:0.15 to 1:7:0.5.

Another embodiment of the present invention, provides a process for production of fatty acids, sn-regio mono-acyl-glycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the ratio of the fat to polar organic solvent is in the range of 1:4 to 1:7.

In yet another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the ratio of the fat to water, is 1:0.15 to 1:0.5.

In still another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the enzymatic hydrolysis with lipase is carried out either in a batch reactor, continuous reactor or a semi-continuous reactor.

Another embodiment of the present invention provides a process for production of fatty acids, sn-regio mono-acyl-glycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the enzymatic hydrolysis with lipase is carried out in a continuous reactor with a residence time of 10 to 60 minutes.

In another embodiment of the present invention, there is provided a process for production of fatty acids and glycerol comprising subjecting the hydrolysate comprising fatty acids, sn-regio mono-acylglycerol (MAG), sn-regio diacyl-glycerols (DAG), and glycerol with an ion exchange resin followed by another enzymatic hydrolysis with lipase to obtain a mixture, wherein the mixture comprises fatty acids and glycerol, and wherein the mixture has less than 5% mono-acylglycerol (MAG), wherein the enzymatic hydrolysis with lipase is carried out in a continuous reactor with a residence time of 10 to 150 minutes.

In still another embodiment of the present invention, there is provided a process for production of fatty acids, sn-regio mono-acylglycerol (MAG), sn-regio diacyl-glycerols (DAG), and glycerol, wherein the process comprises preparing a homogeneous mixture of fat, polar organic solvent, and water, and subjecting the homogenous mixture to an enzymatic hydrolysis with lipase to obtain a hydrolysate, and wherein the hydrolysate comprises fatty acids, sn-regio mono-acylglycerol (MAG), sn-regio diacyl-glycerols (DAG), and glycerol, wherein the enzymatic hydrolysis with lipase is carried out in a batch or semi-continuous reactor with a residence time of 0.5 hour to 2 hours.

In another embodiment of the present invention, there is provided a process for production of fatty acids and glycerol comprising subjecting the hydrolysate comprising fatty acids, sn-regio mono-acylglycerol (MAG), sn-regio diacyl-glycerols (DAG), and glycerol with an ion exchange resin followed by another enzymatic hydrolysis with lipase to obtain a mixture, wherein the mixture comprises fatty acids and glycerol, and wherein the mixture has less than 5% mono-acylglycerol (MAG), wherein the enzymatic hydrolysis with lipase is carried out in a batch or semi-continuous reactor with a residence time of 0.5 hour to 24 hours.

Another embodiment of the present invention provides a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG).

In another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the fat is oil.

In yet another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the fat is oil selected from the group consisting of vegetable oil, tree borne oil, microbial oil, animal origin oil, fish oil, castor oil, olive oil, mustard oil, linseed oil, canola oil, coconut oil, coriander oil, corn oil, cottonseed oil, hazelnut oil, olive oil, neem oil, palm oil, peanut oil, rapeseed oil, rice bran oil, safflower oil, soybean oil, sunflower seed oil, and mixtures thereof.

In still another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the fat is selected from the group consisting of saturated fat, unsaturated fat, hydroxyl unsaturated fat, hydroxyl saturated fat, epoxy fat, phospholipids, wax esters, and mixtures thereof.

In yet another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the fat is a fatty acid based polyol esters.

Another embodiment of the present invention, provides a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the polar organic solvent is selected from the group consisting of t-butanol, iso-amyl alcohol, di-acetone alcohol, ethanol, propanol, and t-pentanol, and mixtures thereof.

In yet another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the enzymatic hydrolysis with lipase is carried out with immobilized lipase.

In another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the enzymatic hydrolysis with lipase is carried out with immobilized lipase immobilized on a support, wherein the base material of the support is selected from the group consisting of co-polymer of polystyrene and divinyl benzene, polyacrylic, polystyrene, and polymethacrylate.

In yet another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the ion exchange resin is a strongly acidic cation exchange resin.

Another embodiment of the present invention provides a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the ion exchange resin is a strongly acidic cation exchange resin selected from the group consisting of sulphonated polymeric resins, Indion130, Indion140, Indion190, Indion770, DIAION® SK1B, DIAION® SK104, DIAION® SK110, DIAION® SK112, DIAION® SK116, DIAION® PK208, DIAION® PHK212, DIAION® PK216, DIAION® PK220, DIAION® PK228, and DIAION® HPK25.

In still another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the enzymatic hydrolysis with lipase is carried out at a temperature ranging from 30° C. to 80° C.

In yet another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the enzymatic hydrolysis with lipase is carried out at a temperature ranging from 50 to 65° C., preferably 60° C.

In another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the homogenous mixture comprises fat, a polar organic solvent and water in the ratio of 1:4:0.15 to 1:7:0.5.

In yet another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the ratio of the fat to polar organic solvent is in the range of 1:4 to 1:7.

In still another embodiment of the present invention, there is provided a process for production of fatty acids, sn-regio mono-acylglycerol (MAG), sn-regio diacyl-glycerols (DAG), and glycerol, wherein the process comprises: preparing a homogeneous mixture of fat, polar organic solvent, and water; subjecting the homogenous mixture to an enzymatic hydrolysis with lipase to obtain a hydrolysate, and wherein the hydrolysate comprises fatty acids, MAG, DAG, and glycerol; and processing the hydrolysate using an ion exchange resin followed by another enzymatic hydrolysis with lipase to obtain a mixture, wherein the mixture comprises fatty acids and glycerol, and wherein the mixture has less than 5% mono-acylglycerol (MAG), wherein the ratio of the fat to water, is 1:0.15 to 1:0.5.

The process of the present invention will now be described in detail.

A fat, oil, or mixture thereof was mixed with water and polar organic solvent to form a single phase system. This signal phase system thus formed referred as homogenous substrate mixture. The homogenous substrate mixture thus obtained may be optionally subjected to pre-treatment by passing through a packed bed of adsorbent to remove enzyme inhibitor specifically lipase inhibitor, whereby the lipase inhibiting constituents present in the oil, are selectively adsorbed onto the adsorbent. The removal of these inhibitor constituents, such as aldehydes, ketones and phospholipids etc. ensures repeated use of the immobilized enzyme in subsequent steps, thereby making the process cost-effective. The substrate mixture thus obtained with or without pre-treatment was subsequently hydrolyzed by passing through a first packed bed reactor(s) of immobilized enzymes, or packed bed reactor of immobilized enzymes and adsorbents under controlled temperature and residence time. The hydrolyzed mixture thus obtained was further passed through another packed bed reactor of ion exchange adsorbent under controlled temperature and residence time. This is followed by passage through a second packed bed reactor(s) of immobilized enzymes under controlled temperature and residence time. The resultant product such as fatty acids, sn-regio Monoacylglyecrol (MAG), sn-regio diacyl glycerol and glycerols obtained from the first packed bed reactor(s) of immobilized enzymes or second packed bed reactor(s) of immobilized enzymes was separated using conventional methods such as distillation, crystallization, and adsorptive or chromatographic techniques.

The homogenous substrate mixture, so obtained after the pre-treatment as described above was subsequently passed through a series of packed bed reactors of immobilized lipase(s) and adsorbents to achieve desired hydrolysis (from 66% to 90%) of the oil using suitable immobilized enzyme under conditions of controlled temperature between 30° C. and 80° C. and residence time of 10 to 150 minutes. This is followed by passage through a second packed bed reactor(s) of immobilized enzymes under controlled temperature between 20° C. to 80° C. and a residence time of 5 to 60 minutes. The resultant product such as fatty acids, sn-regio Monoacylglyecrol (MAG) and glycerols obtained from the first packed bed reactor(s) of immobilized enzymes or second packed bed reactor(s) of immobilized enzymes was separated using conventional methods such as distillation, crystallization, and adsorptive or chromatographic techniques.

The present invention achieves more that 99% conversion of triglycerides with 95% yield of free fatty acids by subjecting the partially hydrolyzed homogenous mixture to ion exchanger resin followed by passage through another packed bed reactor of any other or same suitable preparation immobilized lipase(s) as used in the step described above under controlled temperature and time conditions.

The processes as described in the prior arts are unable to achieve near 100% conversion with any known enzyme and that to achieve near 100% conversion, the time required would be too large to be feasible for commercial applications. In contrast, the hydrolysis process as disclosed in the present invention results in more than 99% hydrolysis of triglycerides with free fatty acid yield of 95% in single phase system and immobilized lipases.

The process as disclosed in the present invention also can be performed using batch semi-continuous or continuous mode.

The batch reaction with 4% enzyme loading in homogenous substrate reaction mixture results in 99% hydrolysis of triglycerides with 80-88% free fatty acids and 12-20% monoglycerides.

The semi-continuous process for oil hydrolysis was carried out in packed bed reactor consisting of immobilized lipase having reaction time of 12 hrs results in 99% hydrolysis of triglycerides with 88% free fatty acids.

The continuous process with immobilized enzyme having residence time 9-15 min results in 99% hydrolysis of triglycerides with 33% free fatty acids and 66% diglycerides yields.

Another embodiment for oil hydrolysis with immobilized lipase column coupled with ion exchange resin column hydrolyses 99% triglycerides with 66% and 33% yield of free fatty acid and monoglycerides respectively within residence time of 90-120 minutes.

The continuous process for oil hydrolysis employing three coupled column of immobilized lipases, ion exchange resin hydrolyses 99% triglycerides with yield of 95% for free fatty acid yields and 5% for monoglycerides.

The resulting product stream from the first enzyme reactor, or the final enzyme reactor, can be separated into sn-regio MAG isomers and free fatty acid by methods such as distillation, crystallization, and/or adsorptive or chromatographic techniques. The process of the present invention thus enables production of free fatty acids, sn-regio MAG isomers, as well as glycerol for various industrial applications.

Minor compounds in oils and fats, such as lipid hydroperoxides, phospholipids, emulsifiers, chlorophyll, carotenoids, lipid polymers, heavy metal ions and even some antioxidants, have deleterious effects on the stability of lipase(s) used for the hydrolysis reactions (Xu et al., *Stability and Stabilization of Biocatalysts*, Amsterdam: Elsevier Science, 1998, pp. 441-446). It is therefore essential to remove these lipase Inhibiting constituents by pretreating with adsorbents in a column reactor. The removal of the minor compounds ensures repeated use of the subsequently employed enzyme reactors, thereby making the process cost-effective.

The fats and oils described in the present invention include but not limited to ordinary vegetable and animal fats and oils as well as processed fats and oils and mixtures of them. Examples of them include but not limited to soybean oil, castor oil, cotton seed oil, mustard oil, linseed oil, rape oil, olive oil, corn oil, coconut oil, safflower oil, palm oil, olive oil, tsubaki oil, sasanqua oil, beef tallow, lard and fish oils, sal fat, illippe butter, kokum butter, shea butter, mowrah fat, phulwara butter, borneo tallow and those fractionated from them and any oil derived from plant origin/animal origin/microbial origin (prokaryotic/eukaryotic) Also the oleo chemical such as fatty acid based polyol esters such as pentaerythritol tetramonoricinoleate, trimethyl propane oleic acid esters etc can be included as oil based feedstock for enzymatic hydrolytic process.

According to the process of the present invention, an immobilized lipase used in the invention can be any preparation commercially available, or prepared specifically, and proven to be suitable for the present invention. The suitability of the preparation herein implies stable and long life to make the process economical.

The lipases produced by microorganisms such as *Thermomyces lanuginosus*, *Rhizopus* including *Rhizopus dele-* mar and, *Rhizopus japonicus, Aspergillus, Candida* including *Candida antarctica* and *Mucor* such as *Mucor japonicus*. Pancreas lipase also can also be used. These lipases are available in the market. The specific lipase cloned in *Yarrowia* spp. and expressed in suitable host can be also be used.

The polar organic solvents described in the hydrolysis reaction according to the present invention are polar organic solvent inert to lipases. Examples of the polar organic solvent includes but not limited to t-butanol, iso-amyl alcohol, di-acetone alcohol, ethanol, propanol, and t-pentanol and different combinations of above solvents.

Examples of a packed bed of adsorbent utilized for pre-treatment of oil includes but not limited to, Diaion® HP2MG, or HPA-75, or HPA-25, or WK10, or WA11; or Sepabeads® SP207 or SP700.

Examples of ion exchange resins includes but not limited to sulphonated polymeric resins such as, but not limited to, Indion130, 140, 190, or 770, Indion FFIP, NIP, GS 300/400, Indion 204, 214, 234, 284/294, 404, 414; DIAION® SKIB, SK104, SK110, SK112, SK116, PK208, PHK212, PK216, PK220, PK228, and HPK25.

Thus, the process of oil and/or fat hydrolysis as disclosed in the present invention, employs mixing oil and/or fat, a polar organic solvent, and water to form single phase system of a homogeneous substrate mixture which is passed through a series of operations on packed bed, continuous or batch mixed reactors containing immobilized lipase(s); adsorption systems; and/or solid catalyzed reactors, to obtain high yield of oleochemicals including free fatty acids, glycerols and/or sn-regio MAG isomers.

The inventors observed that a single phase system obtained by mixing oil, fat or mixture thereof with water and polar organic solvent when subjected to enzymatic hydrolysis, increases hydrolysis of oil or fats to >99% with not less than 95% yield of free fatty acids and glycerol. The high yield and purity of oleo-chemicals such as free fatty acids, glycerols and/or sn-regio MAG isomers obtained within remarkably short period of time.

According to the process disclosed in the invention, oil and water which are immiscible in each other are mixed in polar organic solvent. The three components are mixed to form a single phase system in a certain range of proportions. The mutual solubility of these three components with each other forms the basis of a single phase substrate mixture. Addition of polar organic to the oil-water two phase system is a novel approach disclosed in the present invention to carry out hydrolysis of oil using immobilized lipase.
Use of Specific and Non-Specific Immobilized Lipases Novozym® 435 (Sigma Chemicals, L4777), Lipase acrylic resin from *Candida antarctica* and Immobilized Lipolase® 100 L (HypLIP) (Sigma Chemical Co. L0777) 1,3-specific Lipase from *Thermomyces lanuginosus* were evaluated for the hydrolysis reaction disclosed in the present invention.

Polar organic solvents, t-butanol, iso-amyl alcohol, di-acetone alcohol, ethanol, propanol, t-pentanol, have been evaluated for the reaction. T-butanol was observed to yield highest % conversions with both the enzymes.

The process of the present invention can be extrapolated to both batch and continuous mode with suitable changes in the mode of operation. Also the organic solvent is recovered which can be recycled and reused.

Suitable embodiments of the present invention are now described. While specific configurations and arrangements are discussed, it should be understood that this is done for illustrative purposes only. A person skilled in the relevant art will recognize that other configurations and arrangements can be used without departing from the spirit and scope of the invention. As such, the spirit and scope of the appended claims should not be limited to the description of the preferred embodiment contained therein.

Although the subject matter has been described in considerable detail with reference to certain preferred embodiments thereof, other embodiments are possible. As such, the spirit and scope of the appended claims should not be limited to the description of the preferred embodiment contained therein.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1

Batch Process—t-Butanol as Solvent for Hydrolysis

1) Oil as Substrate: ~80-88% Conversion in 24 hrs
  a. Formation of Fatty Acids and Monoglycerides In a 100 ml reaction flask with 1 g of different immobilized lipases, 10 g of castor oil is added to t-buatnol and water (in ratio of 1:4:0.15) to form the homogenous reaction mixture. The substrate mixture was maintained at 60° C. (the experiment can similarly be carried out for 50° C. and 55° C.) on an orbital shaker and the reaction was monitored for 24 hours by means of acid value. At the end of 24 hours the triglyceride conversion obtained was found to be 99%, whereas % conversions of oils to fatty acids and monoglycerides were 80-88% and 12-20% respectively.

b. Formation of Fatty Acids and Glycerol

Figure 3:
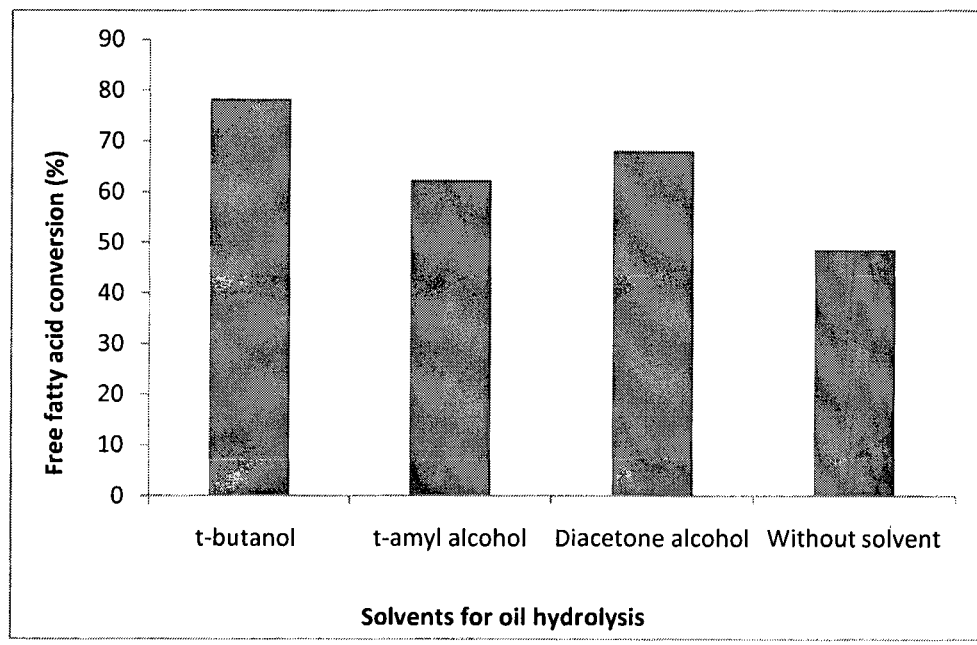
FIG. 3 shows the free fatty acid conversion (%) obtained after 6 hrs under batch conditions using HypLIP (immobilized *Thermomyces langinousa* lipase) without solvent and in different polar organic solvents.

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

2) Fat as Substrate: ~70-80% Conversion in 24 hrs
  a. Formation of Fatty Acids and Monoglycerides In a 100 ml reaction flask with 1 g of different immobilized lipases, 10 g of tristrearin is added to t-butanol and water (in ratio of 1:6:0.15) to form the homogenous reaction mixture. The substrate mixture was maintained at 60° C. (the experiment can similarly be carried out for 50° C. and 55° C.) on an orbital shaker and the reaction was monitored for 24 hours by means of acid value. At the end of 24 hours the triglyceride conversion obtained was found to be 99%, whereas % conversions of oils to fatty acids and monoglycerides were 74% and 26% respectively.

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

3) Oil and Fat as Substrate: ~80-88% Conversion in 24 hrs
a. Formation of Fatty Acids and Monoglycerides In a 100 ml reaction flask with 1 g of immobilized lipase (HypLIP), 10 g of palm oil and tristrearin (in ratio of 1:1) was added to t-butanol and water (in ratio of 1:4:0.25) to form a homogenous reaction mixture. The substrate mixture was maintained at 60° C. (the experiment can similarly be carried out for 50° C. and 55° C.) on an orbital shaker and the reaction was monitored for 24 hours by means of acid value. At the end of 24 hours the triglyceride conversion obtained was found to be 99%, whereas % conversions of oils to fatty acids and monoglycerides were 84% and 16% respectively.

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

Batch Process—Iso-Amyl Alcohol as Solvent for Hydrolysis

1) Oil as Substrate: ~65-70% Conversion in 24 hrs
a. Formation of Fatty Acids and Monoglycerides In a 100 ml reaction flask with 1 g of immobilized *Thermomyces langinousa* lipase (HypLIP), 10 g of castor oil was added to iso-amyl alcohol and water (in ratio of 1:5:0.15) to form a homogenous reaction mixture. The substrate mixture was maintained at 60° C. (the experiment can similarly be carried out for 50° C. and 55° C.) on an orbital shaker and the reaction was monitored for 24 hours by means of acid value. At the end of 24 hours the triglyceride conversion obtained was found to be 99%, whereas % conversions of oils to fatty acids and monoglycerides were 68% and 32% respectively.

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

2) Fat as substrate: ~62-68% Conversion in 24 hrs
a. Formation of Fatty Acids and Monoglycerides In a 100 ml reaction flask with 1 g of immobilized lipase (HypLIP), 10 g of tristrearin was added iso-amyl alcohol and water (in ratio of 1:6:0.2) to form a homogenous reaction mixture. The substrate mixture was maintained at 60° C. (the experiment can similarly be carried out for 50° C. and 55° C.) on an orbital shaker and the reaction was monitored for 24 hours by means of acid value. At the end of 24 hours the triglyceride conversion obtained was found to be 99%, whereas ° A) conversions of oils to fatty acids and monoglycerides were 64% and 36% respectively.

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

3) Oil and Fat as Substrate: ~60-65% Conversion in 24 hrs
a. Formation of Fatty Acids and Monoglycerides In a 100 ml reaction flask with 1 g of immobilized lipase (HypLIP), 10 g of palm oil and tristrearin was added iso-amyl alcohol and water (in ratio of 1:4:0.2) to form a homogenous reaction mixture. The reaction mixture was maintained at 60° C. (the experiment can similarly be carried out for 50° C. and 55° C.) on an orbital shaker and the reaction was monitored for 24 hours by means of acid value. At the end of 24 hours the triglyceride conversion obtained was found to be 99%, whereas % conversions of oils to fatty acids and monoglycerides were 65% and 35% respectively.

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

The percent conversion of oil and/or fat using the process described above was compared with the prior art. The Comparative analysis is provided in Table 1.

Example 2

Semi-Continuous Process

Figure 4:
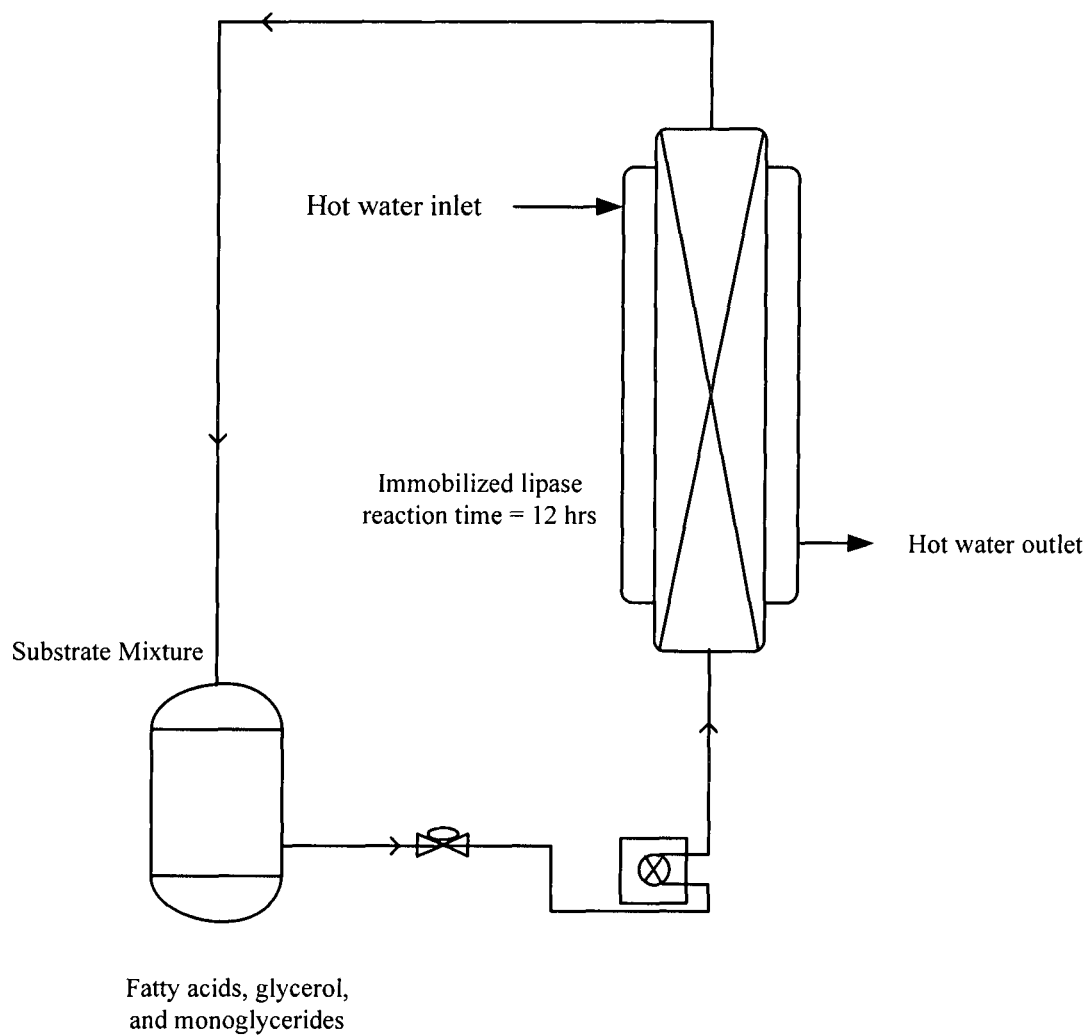
FIG. 4 shows the scheme for semi-continuous process for oil hydrolysis.
Figure 7:
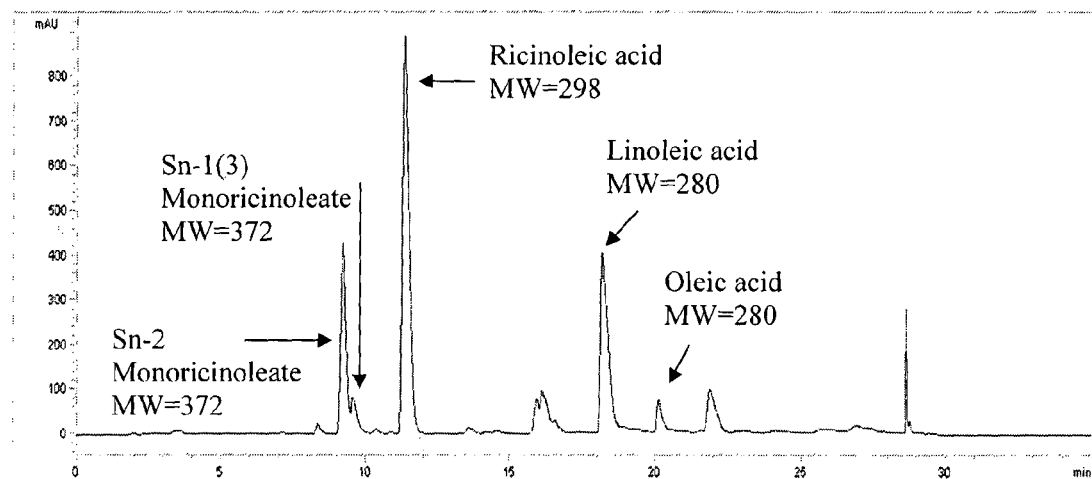
FIG. 7 shows the HPLC-MS profile of hydrolytic products from immobilized lipase column.

1) Single Column: ~88% Conversion in 12 hrs
a. Formation of Fatty Acids and Monoglycerides The continuous process for oil hydrolysis was carried out in packed bed reactor (PBR) consisting of jacketed glass columns maintained at 60° C. The experiment can similarly be carried out for 50° C. and 55° C. PBR containing 1, 3 specific enzyme immobilized on a methacrylate support (volume of 50 ml) was fed with substrate mixture containing castor oil, t-butanol and water (in ratio of 1:6:0.15) which was continuously stirred with help of magnetic stirrer. The substrate mixture was recycled through the PBRs for 12 hours. The triglyceride conversion obtained was 99%, whereas % conversion of oils to fatty acids was 88% with 12% unreacted monoglycerides. The products formed were fatty acids, glycerol and monoglycerides. FIG. 4 shows scheme for semi-continuous process for oil hydrolysis. 99% splitting of castor oil with 88% free fatty acid yield can be obtained from the scheme described herein. (FIG. 7). Castor oil hydrolytic products like mono ricinoleate along with ricinoleic acid are observed as major products. Other fatty acids can also be observed in the profile.

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

Example 3

Continuous Process

Figure 5:
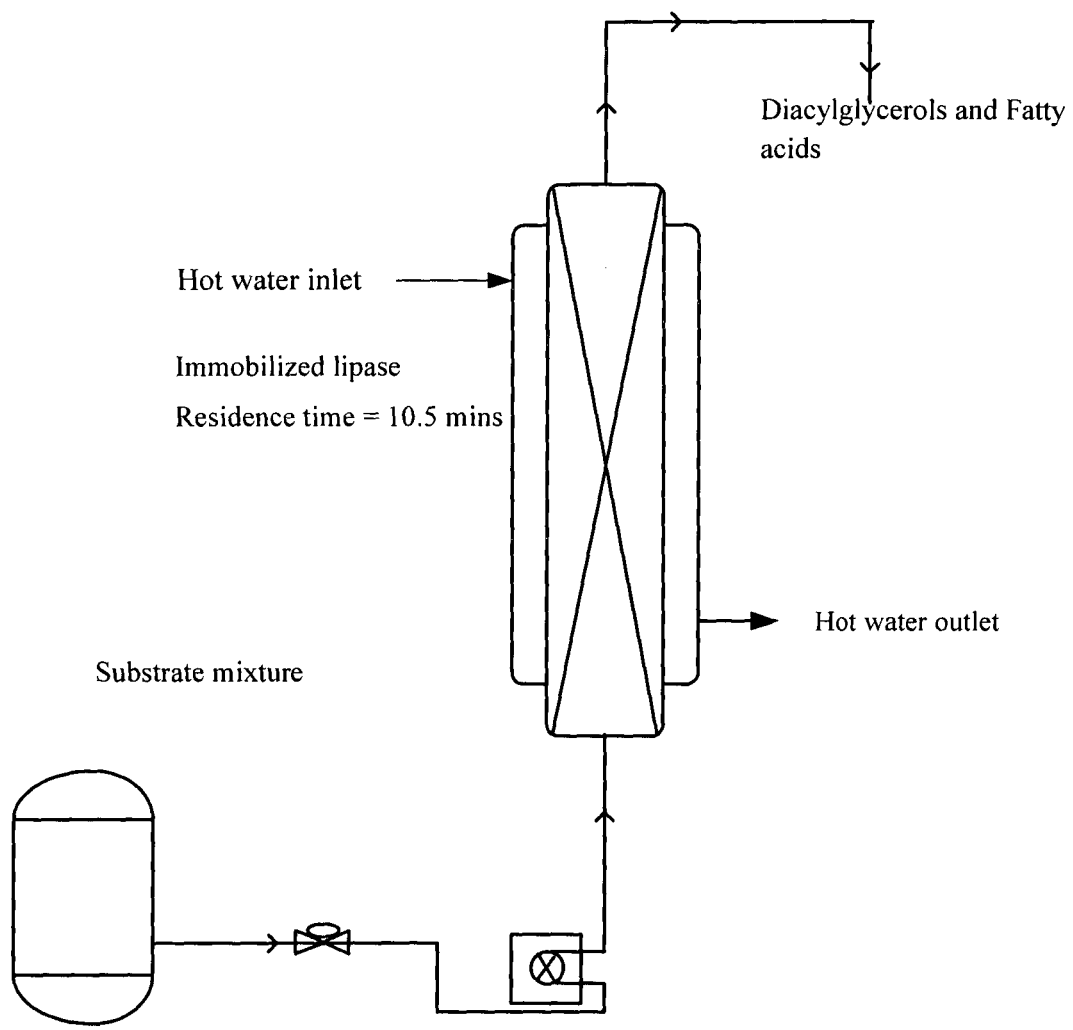
FIG. 5 shows the scheme of continuous process for production of diacylglycerol and fatty acids.

1) Single Column: 30-33% Conversion <10-15 Minutes a. Formation of Fatty Acids and Monoglycerides The continuous process for oil hydrolysis was carried out in a packed bed reactor consisting of jacketed glass column maintained at 60° C. (the experiment can similarly be carried out for 50° C. and 55° C.) containing 1,3 specific enzyme immobilized on a methacrylate support. The reaction mixture as described in above examples was feed into the PBR and residence time was maintained in the range of 9 to 15 minutes. The yield of triglyceride hydrolysis is more than 99% and a yield of 33% is observed for free fatty acids. The diacylglycerols thus formed can be further separated from fatty acids (FIG. 5).

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

Figure 6:
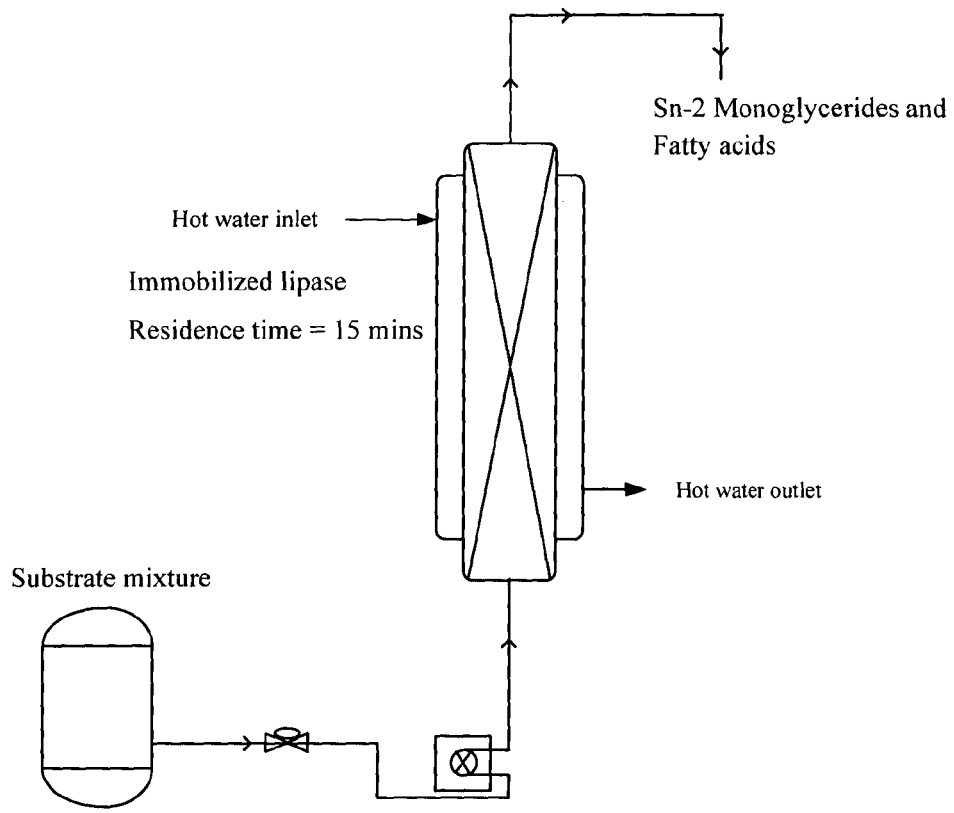
FIG. 6 shows the process for production of sn-2 monoglycerides and fatty acids.

2) Single Column: 66-70% Conversion in 15 Minutes a. Formation of Fatty Acids and Monoglycerides The continuous process for oil hydrolysis was carried out in a packed bed reactor consisting of jacketed glass column maintained at 60° C. (the experiment can similarly be carried out for 50° C. and 55° C.) containing 1,3 specific enzyme immobilized on a methacrylate support. The reaction mixture as described in above examples was feed into the PBR and residence time was maintained in the range of 15-20 minutes. The yield of oil hydrolysis was obtained to be more than 99% while that for free fatty acid was recorded to be 66%. The sn-2 monoglycerides and fatty acids can be further separated (FIG. 6).

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

Example 4

Figure 8:
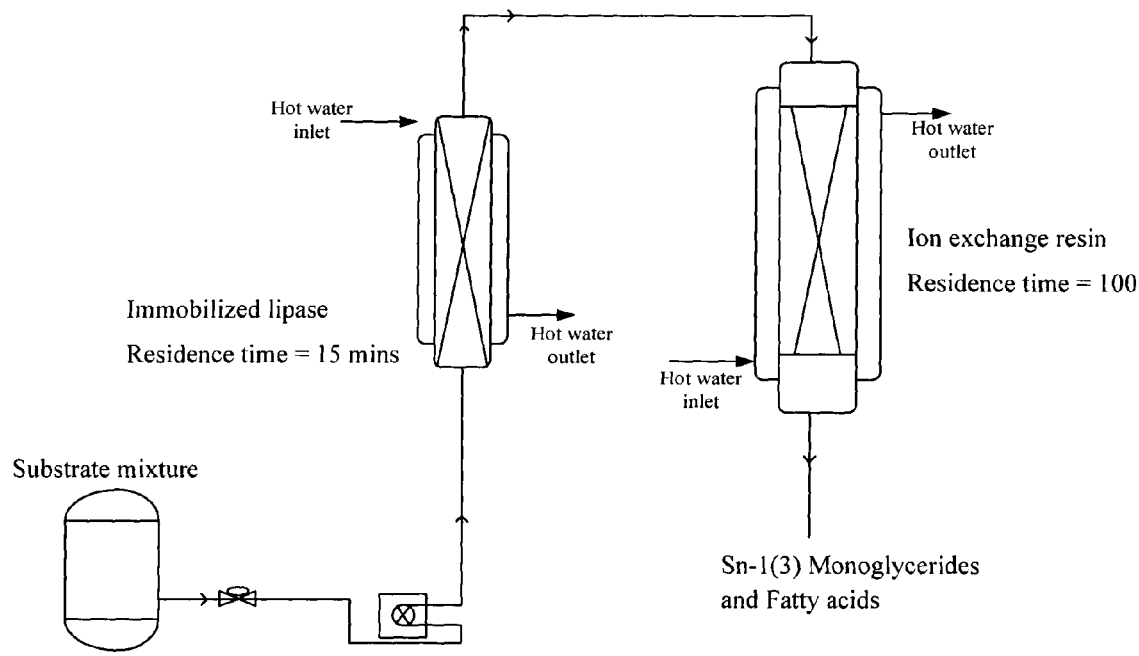
FIG. 8 shows the two-step scheme for oil hydrolysis resulting in the production of sn-1(3) Monoglycerides and fatty acids.
Figure 9:
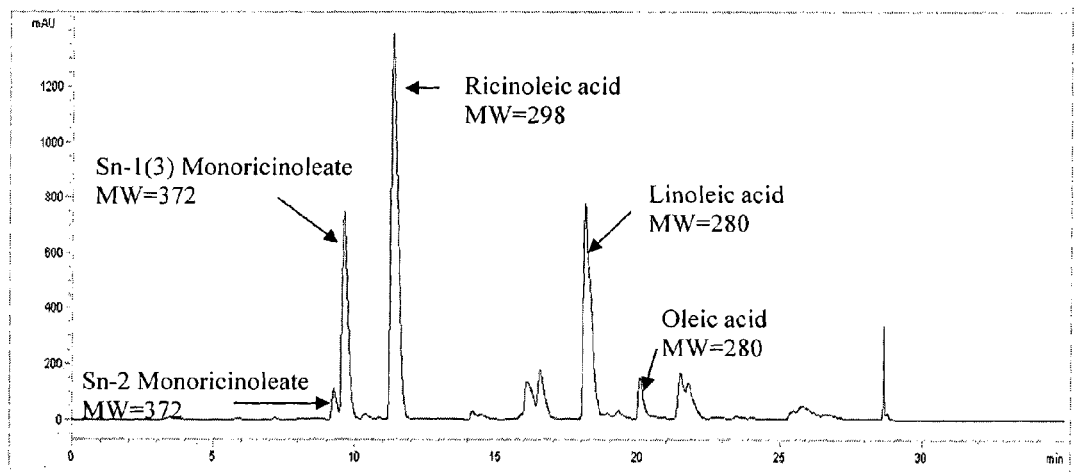
FIG. 9 shows the HPLC-MS profile of hydrolytic products from rearrangement column.

Single Column+Adsorbent for Rearrangement: 66-70% Conversion in 115 Minutes a. Formation of Fatty Acids and Monoglycerides The continuous process for oil hydrolysis was carried out in a packed bed reactors consisting of jacketed glass column maintained at 60° C. (the experiment can similarly be carried out for 50° C. and 55° C.) containing immobilized lipase and adsorbent. The reaction mixture as described in above examples was feed into the 1st PBR of Immobilized lipase for 15 minutes followed by 90-120 minutes in 2nd PBR of adsorbent for rearrangement (FIG. 8). This resulted in 99% triglyceride hydrolysis with 66-70% yield for free fatty acids and contains ⅓-MAG and fatty acids. Castor oil hydrolytic products like sn-1(3) mono ricinoleate were observed as major products. Ricinoleic acid can also be observed in the profile. (FIG. 9).

b. Formation of Fatty Acids and Glycerol

The reaction was repeated with lipase enzymes HypLIP (Indigenously immobilized Lipolase® 100L), Lipozyme® TL IM (Immobilized Lipolase® 100L), Lipozyme® RM IM Novozym® 435 and lipase from *Pseudomonas cepacia* acting on the hydrolysis products produced after the first enzymatic hydrolysis reaction. FIG. 1 shows the profile for percent hydrolysis of castor oil in homogenous media. FIG. 3 shows the free fatty acid conversion (%) obtained after 6 hrs under batch conditions using HypLIP) without solvent and in different polar organic solvents. HypLIP shows high initial rates of conversion when compared to any of the other enzyme preparations used for the study.

Example 5

Dual Column+Adsorbent for Rearrangement: 88-95% Conversion in 140 Minutes a. Formation of Fatty Acids and Monoglycerides The continuous process for oil hydrolysis was carried out in series of packed bed reactor consisting of jacketed glass columns maintained at 60° C. The experiment can similarly be carried out for 50° C. and 55° C. $1^{st}$ PBR containing 1, 3 specific enzyme immobilized on a methacrylate support (volume of 50 ml) was feed with reaction mixture as in Example 1a. The residence time was in the range of 3 to 100 minutes.

a. Formation of Fatty Acids and Glycerol

Figure 10:
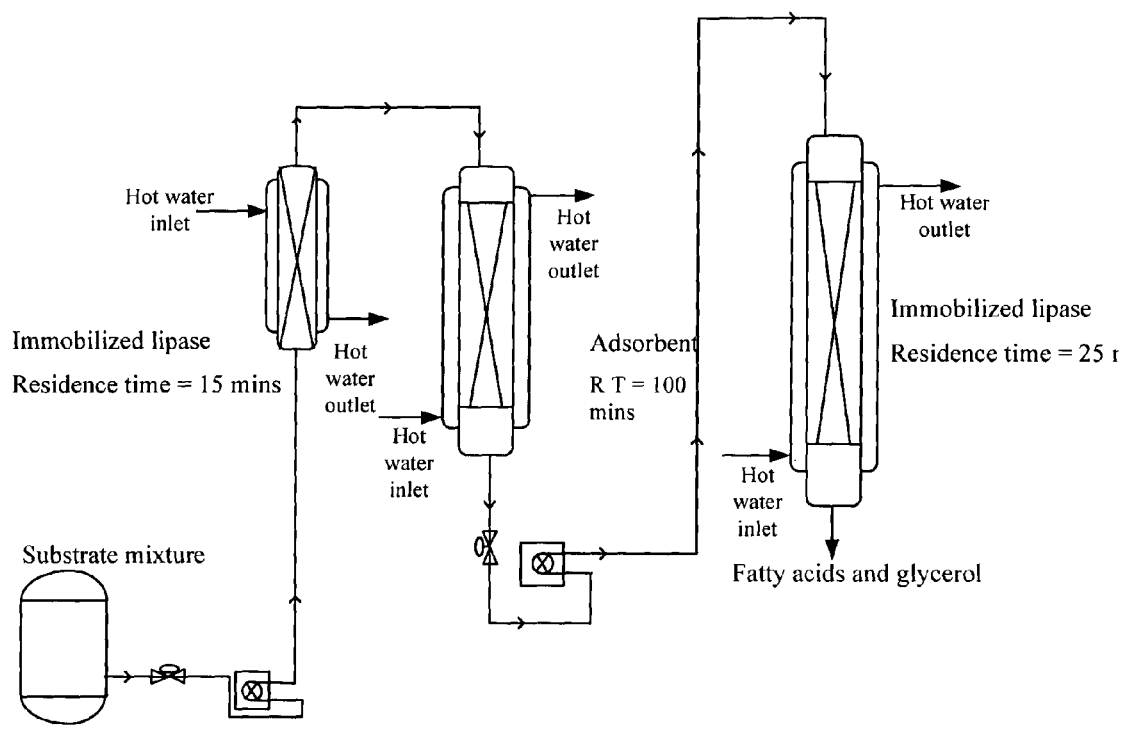
FIG. 10 shows the three step PBR scheme for oil hydrolysis resulting in the production of fatty acids and glycerol.

The product mixture of $1^{st}$ PBR was feed into $2^{nd}$ PBR containing adsorbent for rearrangement (volume of 100 ml)

with residence time in the range 40 to 120 minutes. The product stream from 2$^{nd}$ PBR was then allowed to pass into 3$^{rd}$ PBR containing immobilized 1, 3 specific enzyme (volume of 25 ml) having residence time in the range of 5 to 50 minutes. The three step PBR scheme for oil hydrolysis results in a complete conversion of triacylglycerol into fatty acids and glycerol. The residence time of 140 minutes yields more than 95% free fatty acids and resultant products i.e. fatty acids and glycerol can be further separated (FIG. 10).

TABLE 1

Comparative analysis of hydrolysis of oil using lipases

| S. No. | Reaction system | Lipase source | Substrate | Maximum hydrolysis | Reference |
|---|---|---|---|---|---|
| 1 | Two phase (buffer/isooctane): batch reaction | *Mucor miehei* | Blackcurrant seed oil | 75% (4 hrs) | Vacek et al., *Enzyme and Microbial Technology*, 27 (2000), pp. 531-536 |
| 2 | Chemically-modified AOT/isooctane reverse micelles | *Candida rugosa* | Olive oil | 36% (72 hrs) | He et al., *Biotechnology Letters*, 23 (2001), pp. 1257-1262 |
| 3 | Two phase batch reaction | *Candida cylindracea* | Rice bran oil | 70% (5 hrs) | Murty et al., *Biotechnology Letters*, 26 (7) 2004, pp. 563-567 |
| 4 | Two phase batch reaction | *Thermomyces lanuginosa* | Soybean oil | 70% (24 hrs) | Freitas et al., *World J Microbiol Biotechnol*, 23 (2007), pp. 1725-1731 |
| 5 | Biphasic system (water in oil dispersion) | *Candida rugosa* | Castor oil | 80% (48 hrs) | Sirshendu De et al., *Biotech Bioprocess engineering*, 14 (2009), pp. 200-224 |
| 6 | Biphasic batch system | *Candida rugosa* | Salmon oil | 91% (24 hrs) | Xuebing Xu et al., *The Open Biotechnology Journal*, 4 (2010), pp. 47-55 |
| 7 | Biphasic batch system | *Thermomyces lanuginosus* | Soybean oil | 89% (48 hrs) | Cavalcanti-Oliveira et al., *Enzyme Research Volume 2011* |
| 8 | Single phase system | *Candida antarctica* | Castor oil | 90% (24 hrs) | Present invention |

We claim:

1. A process for production of fatty acids, sn-regio monoacylglycerol (MAG), sn-regio diacyl-glycerols (DAG), and glycerol, comprising:
    preparing a homogenous mixture of fat, polar organic solvent, and water, wherein the homogenous mixture is prepared by mixing the fat, a polar organic solvent and water in a ratio of 1:4:0.15 to 1:7:0.5 under conditions to form a single phase system;
    subjecting the homogenous mixture to a first enzymatic hydrolysis with an immobilized lipase to obtain a partial hydrolysate comprising fatty acids, MAG, DAG, and glycerol;
    subjecting the partial hydrolysate to an ion exchange resin to obtain a first product comprising MAG and DAG; and
    subjecting the first product to a second enzymatic hydrolysis with the immobilized lipase to obtain a second product comprising fatty acids, glycerol, and less than 5% MAG,
    wherein said polar organic solvent is selected from the group consisting of t-butanol, iso-amyl alcohol, di-acetone alcohol, ethanol, propanol and t-pentanol.

2. The process as claimed in claim 1, wherein said fat is oil.

3. The process as claimed in claim 2, wherein said oil is selected from the group consisting of vegetable oil, tree borne oil, microbial oil, animal origin oil, fish oil, castor oil, olive oil, mustard oil, linseed oil, canola oil, coconut oil, coriander oil, corn oil, cottonseed oil, hazelnut oil, olive oil, neem oil, palm oil, peanut oil, rapeseed oil, rice bran oil, safflower oil, soybean oil, sunflower seed oil, and mixtures thereof.

4. The process as claimed in claim 1, wherein said fat is selected from the group consisting of saturated fat, unsaturated fat, hydroxyl unsaturated fat, hydroxyl saturated fat, epoxy fat, phospholipids, wax esters, and mixtures thereof.

5. The process as claimed in 1, wherein said fat is a fatty acid based polyol esters.

6. The process as claimed in claim 1, wherein the lipase is immobilized on a support, wherein the base material of the support is selected from the group consisting of co-polymer of polystyrene and divinyl benzene, polyacrylic, polystyrene, and polymethacrylate.

7. The process as claimed in claim 1, wherein the ion exchange resin is a strongly acidic cation exchange resin.

8. The process as claimed in claim 1, wherein the first enzymatic hydrolysis with immobilized lipase is carried out at a temperature ranging from 30° C. to 80° C.

9. The process as claimed in claim 8, wherein the first enzymatic hydrolysis with the immobilized lipase is carried out at a temperature ranging from 50 to 65° C.

10. The process as claimed in claim 8, wherein the first enzymatic hydrolysis with the immobilized lipase is carried out at a temperature of 60° C.

11. The process as claimed in claim 1, wherein said process results in more than 99% conversion of said fat to fatty acids, MAG, DAG and glycerol.

12. The process as claimed in claim 1, wherein at least one of the first or second enzymatic hydrolysis with immobilized lipase is carried out either in a batch reactor, continuous reactor or a semi-continuous reactor.

13. The process as claimed in claim 1, wherein the first enzymatic hydrolysis with immobilized lipase is carried out in a continuous reactor with a residence time of 10 to 60 minutes.

14. The process as claimed in claim 1, wherein the second enzymatic hydrolysis with immobilized lipase is carried out in a continuous reactor with a residence time of 10 to 150 minutes.

15. The process as claimed in claim 1, wherein the first enzymatic hydrolysis with immobilized lipase is carried out in a batch or semi-continuous reactor with a residence time of 0.5 hour to 2 hours.

16. The process as claimed in claim 1, wherein the second enzymatic hydrolysis with immobilized lipase is carried out in a batch or semi-continuous reactor with a residence time of 0.5 hour to 24 hours.

* * * * *